United States Patent [19]

Schael

[11] 4,252,115
[45] Feb. 24, 1981

[54] APPARATUS FOR PERIODICALLY RINSING BODY CAVITIES, PARTICULARLY THE ABDOMINAL CAVITY

[75] Inventor: Wilfried Schael, Bad Homburg, Fed. Rep. of Germany

[73] Assignee: Dr. Eduard Fresenius, Chemisch-pharmazeutische Industrie KG. Apparatebau KG., Bad Homburg, Fed. Rep. of Germany

[21] Appl. No.: 966,496

[22] Filed: Dec. 4, 1978

[30] Foreign Application Priority Data

Dec. 9, 1977 [DE] Fed. Rep. of Germany ....... 2754809

[51] Int. Cl.³ .............................................. A61J 7/00
[52] U.S. Cl. .................................. 128/213 A; 210/649
[58] Field of Search ........................... 128/213, 214 R; 417/477; 210/321 A, 321 B, 23 R

[56] References Cited

U.S. PATENT DOCUMENTS

| | | | |
|---|---|---|---|
| 3,520,298 | 7/1970 | Lange | 128/213 A |
| 3,709,222 | 1/1973 | DeVries | 128/213 A |
| 3,927,955 | 12/1975 | Spinosa et al. | 417/477 |
| 3,942,915 | 3/1976 | Thomas | 417/477 |
| 4,012,176 | 3/1977 | Drori | 417/477 |
| 4,060,348 | 11/1977 | Bianca | 417/477 |
| 4,096,859 | 7/1978 | Agarwal et al. | 128/213 A |
| 4,108,575 | 8/1978 | Schäl | 417/477 |
| 4,190,047 | 2/1980 | Jacobsen et al. | 128/213 A |

FOREIGN PATENT DOCUMENTS 2535650 10/1977 Fed. Rep. of Germany ........... 417/477

*Primary Examiner*—Robert W. Michell
*Assistant Examiner*—Thomas Wallen
*Attorney, Agent, or Firm*—W. G. Fasse; D. F. Gould

[57] ABSTRACT

Apparatus for rinsing body cavities includes a double tube pump (1) for simultaneously pumping fluid into a storage vessel (4) for subsequent feed through a catheter (K) and pumping discharged fluid from a measuring vessel (9) at the same rate, so that surplus fluid with the discharge can be measured. The measuring vessel has sensors (11,12) which switch on and switch off the pump when fluid in the measuring vessel falls or rises to predetermined levels. An additional pump (13) may be provided for the surplus fluid extraction. The double tube pump comprises a pair of parallel identical tubes (24a, 24b) with joined end connections (34,35) in a stator (21) which are squeezed by common rollers (32) mounted in a rotor (27).

(FIG. 1)

10 Claims, 4 Drawing Figures

APPARATUS FOR PERIODICALLY RINSING BODY CAVITIES, PARTICULARLY THE ABDOMINAL CAVITY

BACKGROUND OF THE INVENTION

The invention relates to an apparatus for repeatedly rinsing body cavities with sterile fluids by periodic filling and emptying, with measurement of the additional quantity of fluid removed from the cavity. Some examples of its application are peritoneal dialysis and rinsing of the bladder. The description which follows relates particularly to use in peritoneal dialysis.

The normal process of peritoneal dialysis consists of introducing a certain quantity of a rinsing fluid through a catheter inserted in the body cavity of the patient, then emptying it again, possibly after waiting for a certain time. The process is repeated several times in the course of a treatment. Due to osmotic effects the quantity of fluid flowing out is generally somewhat larger than the quantity introduced. Measurement of the additional quantity of fluid flowing out is of considerable interest in appraising the treatment.

In known peritoneal dialysis machines some do not attempt to draw up a balance, i.e. do not ascertain the additional quantity of fluid removed. Some machines draw up a balance by measuring the quantity of fluid supplied and the quantity removed in two identical measuring vessels with level electrodes, and by drawing off the excess fluid present separately and collecting it in a third measuring vessel when the discharge vessel is full. However, trouble is liable to occur in measuring the level with the fitted level electrodes, e.g. because of possible foam formation in the measuring chambers, and the fact that the volume introduced is fixed imposes a certain limitation. Another known machine operates with variable volumetric dosing or measurement of the quantities flowing in and out, thus avoiding one disadvantage of the previous machine, although this method has also not proved itself in practice because of the high cost and the likelihood of trouble.

DT-AS 2 101 168 describes a peritoneal dialysis machine in which the fluids flowing in and out are measured in flexible bags located in an enclosed, rigid, water-filled container, so that the sum of the quantities of fluid in both bags is kept constant and the inflow and outflow can be directly compared. A disadvantage of this machine is the manipulation necessary to insert the bags, in view of the requirement that the surrounding container must be completely sealed and completely full of water. This is not very practicable in view of the need to change the bags at every use, since they are components of a once usable tube system.

The invention aims to provide a peritoneal dialysis machine which will enable the additional quantity of fluid flowing out to be ascertained exactly, with simple and easily operated technical means and without any precision measuring instruments.

SUMMARY OF THE INVENTION

According to the invention there is provided an apparatus for rinsing body cavities in which the quantity of the supplied rinsing fluid, the quantity of the discharged fluid, and any surplus fluid are all measured. A double hose pump having an identical conveying capacity in each of its halves, is used for conveying the rinsing fluid and for conveying the discharged fluid. A pump of the single hose type is used for conveying any surplus fluid. A fluid measuring device is operatively arranged to measure the discharged fluid and any surplus fluid and to provide respective control signals for the motors of the pumps.

BRIEF FIGURE DESCRIPTION

The invention will be described with reference to the accompanying drawings, in which.

DETAILED DESCRIPTION OF PREFERRED EXAMPLE EMBODIMENTS AND OF THE BEST MODE OF THE INVENTION

Figure 1:
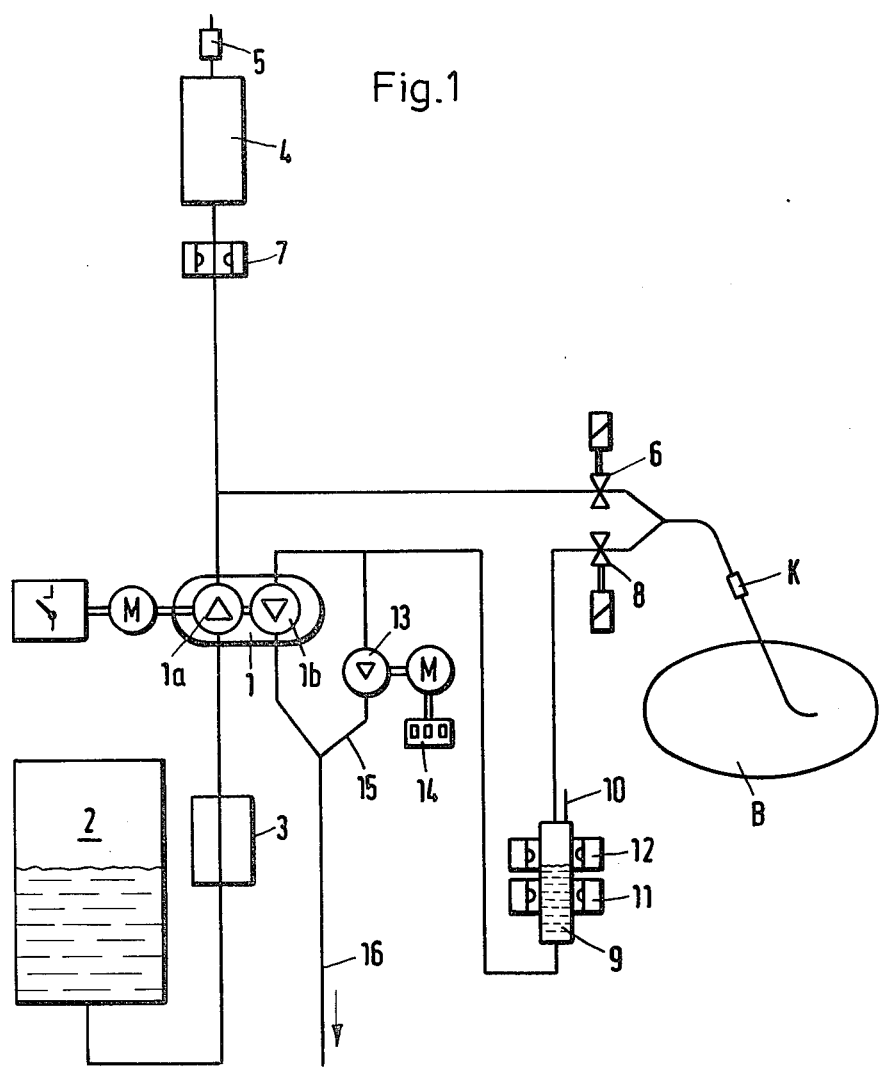
FIG. 1 is a diagrammatic representation of the fluid circuit.

Referring you now to FIG. 1, the dialysis solution is pumped out of a storage container 2 through a warming means 3 and into a vessel 4 by one side 1a of a double tube pump 1. The warming means 3 may e.g. be a coil of tubing with the solution flowing through it, in a thermostatically controlled bath of water, or other known apparatus for warming injection solutions. The vessel 4 may be a bag ventilated by an attached steep filter 5 or another commonly used vessel.

A specific quantity of solution, pumped into the vessel 4, may be fed in by counting a given number of revolutions of the tube pump 1, e.g. through bringing an electrical preselection meter or counter to its initial position when the pump is switched on, so that the pump can be stopped when a predetermined number of pulses has been reached; the pulses may be generated e.g. by a contact maker actuated by the rotor of the pump. This or a similar method of feeding in a given quantity can be applied, since a high degree of absolute accuracy is not necessary in this case, the only requirement being that dosing should be adequately reproducible.

The solution fed into the vessel 4 flows by gravity through the catheter K into the abdominal cavity B of the patient, by opening a hose clip valve 6. The emptying of the vessel 4, and thus the end of the inflow process, may be recognized automatically e.g. by a sensing element 7 in the form of a light or ultrasonic barrier or a capacitative sensor, so that an electrical signal produced thereby can close the valve 6, which is actuated by an electromagnet or other drive means.

For the operation of the system it is not of great importance whereabouts in the line between the vessel 4 and hose clip valve 6 the sensing element is located. It is also possible for the signal indicating the end of the inflow process to be established by measuring or weighing directly at the vessel 4. A logical complement to the system can be obtained by monitoring the duration of the inflow process, so that a warning signal can be produced if a given maximum duration is exceeded. In this way any obstacle to the flow, caused e.g. by blocking of the catheter or kinking of the tube, can be recognized automatically.

The inflow process may be followed by a period of waiting, to allow the fluid introduced to take effect. This can be obtained by switching on a time switch, set to the desired time, at the end of the inflow process.

When the set time has elapsed the switch then produces a switching signal for the next process.

By opening a hose clip valve 8 the fluid then flows by gravity into the measuring chamber 9. This is a component of the tube system and comprises e.g. an inserted piece of tubing with a larger diameter. The measuring chamber is ventilated by a short piece of open pipe 10 and is in a support with means for monitoring the filling level. In the preferred embodiment 2 level sensors 11 and 12 are used, e.g. in the form of light or ultrasonic barriers or capacitative sensors, which produce a signal when the liquid drops below or rises above the level in question.

As soon as the discharged fluid in the measuring chamber 9 has risen to the level of the sensor 12, the signal transmitted by the sensor 12 switches on the pump 1. The conveying speed of the pump is selected so that it is in all cases higher than the maximum expected discharge speed. Consequently, when the pump 1 has been switched on the level in the measuring chamber 9 drops again. As soon as it has dropped to the level of the sensor 11, the signal transmitted by the sensor 11 switches off the pump 1. The liquid in the measuring chamber therefore rises again until the level of the sensor 12 is reached. The pump 1 is then switched on again, and so on.

As an alternative to cyclically pumping the discharge fluid out of the measuring chamber 9 as described, a continuous pumping out process may be applied, with the two level sensors 7 and 12 replaced by a continuous or virtually continuous level measuring device, and with the pump governed by an electronic control with the desired value set, so that the filling level in the measuring chamber is kept approximately constant. This means that the control sets the conveying speed of the pump 1 to make it agree with the inflow speed of fluid into the chamber 9.

While the discharged fluid is being removed, the total quantity conveyed by pump 1 is in all cases measured in accordance with the invention, preferably by counting the number of revolutions of the pump drive, as already described at the beginning in connection with the filling of the vessel 4. As soon as the preselected quantity is reached, i.e. the preselected number of revolutions of the double tube pump 1, the pump is switched off. Assuming both halves 1a and 1b of the double tube pump 1 to have the same conveying capacity, the same quantity of fluid will at this stage be in the vessel 4 ready for the next inflow process. The quantity discharged up to this moment is therefore the same as the quantity which will flow in for the next cycle. The special measures which make the conveying capacity of the two halves 1a and 1b of the pump exactly identical will be described later.

When the pump 1 has pumped the preselected quantity out of the measuring chamber 9, the fluid which is then still flowing out into the chamber constitutes the surplus, which is in addition to the quantity originally passed into the abdominal cavity B and which has to be ascertained separately. In accordance with the invention, this surplus quantity is preferably measured as follows. When the pump 1 has been switched off the pump 13, which is also a tube pump, now takes over the continued removal of fluid from the chamber 9, and control is exercised in the same way by the level sensors 11 and 12. The pump 13 may be coupled to a measuring device to indicate the quantities pumped out by it, e.g. a meter 14 actuated by the same drive. Another possibility is for the outflow pipe 15 of the pump 13 to lead, not into the main outflow pipe 16 as shown in FIG. 1, but into a separate collecting vessel with a volume scale from which the quantity can be read.

In accordance with the invention, the criterion taken for the discharge speed is the time required for the fluid in the measuring chamber 9 to rise from the level sensor 11 to the level sensor 12. This time, which is identical with the stoppage time of the pump 1 or 13 during the discharge process, is inversely proportional to the discharge speed. To find out when the discharge process is completely or at least near enough over, a time switch, for example, is therefore used. When a given maximum time is exceeded, the time switch transmits a signal to indicate the end of the discharge process. This is done by starting the time switch each time the level sensor 11 is reached and setting it back each time the sensor 12 is reached. As soon as the time for the liquid to rise from the sensor 11 to sensor 12 exceeds the predetermined maximum, the switching signal indicates the end of the discharge and the pump 13 is switched on again, to empty the chamber 9 in a defined way to the level of the sensor 11. The signal from the sensor 11 then causes the pump 13 to be switched off and the valve 8 to be closed. The next inflow process follows by opening the hose clip valve 6.

Monitoring of the discharge process in respect of possible blockage of the catheter or other blockage of the flow is likewise provided by monitoring the speed of discharge. An alarm signal is set off if the time taken for the liquid in the chamber 9 to rise from the sensor 11 to the sensor 12 exceeds a given value before the volume discharged has reached the minimum value corresponding to the volume introduced.

Where the other above mentioned process is used, with the fluid being pumped continuously out of the measuring chamber 9 by the pumps 16 and 13, the speed at which the pumps remove it is in direct agreement with the speed of discharge, owing to the continuous level adjustment. Thus, e.g. when D.C. motors are used for the pump drives, the voltage supplied to the motors may be used as an approximate measure of the speed of discharge. A comparator with a time member provided downstream of it may therefore be used to determine the end of discharge. The time member may produce a signal when the voltage supplied to the motor of the pump 13 falls below a minimum value for a given time. A comparator with a time member downstream of it may equally be employed to detect blockage of the catheter or another obstacle in the flow during the discharge process. The time member then produces an alarm signal when the voltage supplied to the motor of the pump 1 is below a predetermined minimum value for a given time.

It is possible to do without the pump 13 and to provide an additional hose clip valve instead. The valve then clamps a tube leading from the measuring chamber 9 to a separate measuring vessel provided with a volume scale. The measuring vessel has to be arranged below the chamber 9. The control for the hose clip valve is similar to that previously described for the pump 13.

An important operating element in the arrangement shown in FIG. 1 is the double tube pump 1. The function of the pump is to make the two volumes of fluid conveyed through its two halves 1a and 1b agree exactly. The difference between them should as far as possible be not more than 0.2% of the total volume conveyed.

It is known that tube pumps of the conventional roller pump construction are suitable for accurate dosing only under certain conditions. The decisive factors are inter alia the tolerances of the internal diameter and thus the internal cross-sectional areas of the tube. Even in the case of tubes made particularly carefully, manufacturers' specifications quote diameter tolerances of the order of 2 to 3% with the usual extrusion process. This in itself gives a deviation of the order of 4 to 6% for the cross-sectional area and thus the volume pumped per unit of time. Considerable deviations may further arise owing to the fact that the way in which the tube is inserted in the head of the pump is not exactly reproducible, e.g. it may be twisted or inserted with a different bias. A further reason for inaccurate dosing is the fatiguing of the tube material in the course of time. The result of this is that when the tube is relaxed it no longer returns completely to its original shape. This represents a reduction in internal cross-sectional area and a decline in pumping capacity. A particularly important factor, finally, is the pressure prevailing at the inlet, from the suction side of the pump. Depending on the elastic properties of the tube, different pressure at the inlet will give a different degree of filling and thus affect the volume conveyed. This effect may become particularly marked when the pressure at the inlet is below atmospheric pressure.

The facts set out do not at first sight provide much prospect of using tube pumps to draw up the required balance, due to the above mentioned requirement that the error in the balance should as far as possible not be more than 0.2%. However, the invention has special features which readily produce the required reduction in this error.

One of these features is that a special tube pump, operating with two pump tubes, is used instead of two individual pumps. This eliminates from the outset any irregularities in the drive and tolerancies in the dimensions of the active components of the pump in respect of their effect on accuracy in drawing up a balance.

A second feature is that the inlet pressures of the two halves of the pump are kept equal by the special conformation of the system shown in FIG. 1. Since the storage container and the measuring chamber 9 are in communication with the atmosphere through a ventilation and are arranged at substantially the same level, there is adequate agreement between the inlet pressures. Fluctuations in pressure, caused by variations in the level of liquid in the storage container 1 and measuring chamber 9, and slight and virtually insignificant.

Figure 2:
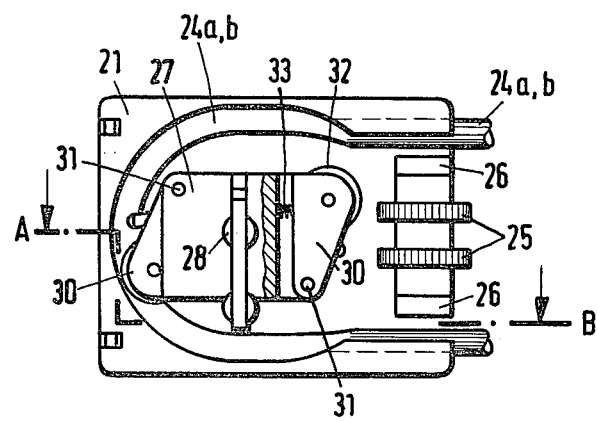
FIG. 2 is a plan view of the pumping head of a double tube pump.
Figure 3:
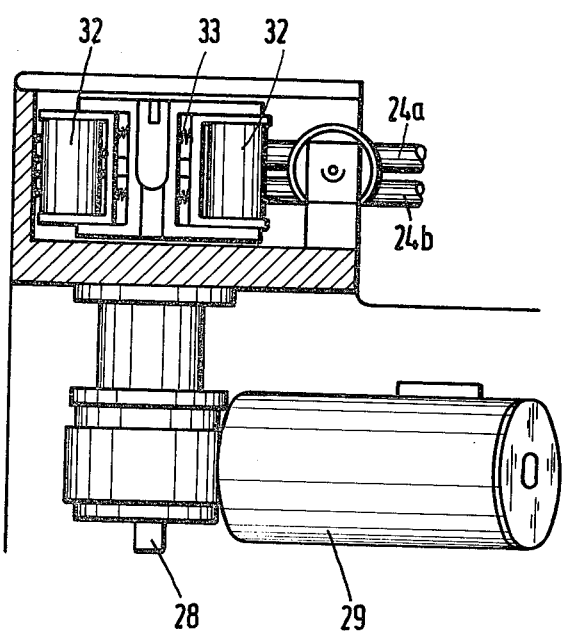
FIG. 3 is a section taken along the line A–B in FIG. 2.

A desirable construction for the double tube pump is illustrated in FIGS. 2 and 3. The head for the pump comprises a stator 21 and a rotor 27. The two tubes 24a and 24b are bent through 180° on insertion in the stator and fit closely against the inner surface thereof. Clamping pieces 26 for fixing the tubes 24a and 24b in the stator 21 are arranged at the open side of the stator and can be operated by milled nuts 25. FIG. 2 shows the clamping pieces before the ends of the tubes are clamped fast.

In the centre of the stator is the rotor 27, which can be rotated via its shaft 28 by a geared motor 29. Two identical levers 30 are fixed to the rotor so each can pivot about a spindle 31. The levers each carry a roller 32, mounted rotatably in their spindle. This rolls along the inserted pump tubes when the rotor turns. At the pressure point between the rollers and the inner surface of the stator, the tubes are compressed sufficiently to close their cross-section at this point, and the rollers push the content of the tubes along the front of themselves by their rolling movement.

The levers 30 are each urged radially outwardly by two biased helical springs 33, the maximum deflection being defined by a stop. By the action of the springs the rollers 32 resiliently fit the wall thickness of the tubes. By appropriate choice of spring force, one can ensure that the tubes used are securely clamped at the pressure point but that overstraining of the tube material is avoided.

The pump described in the example appears particularly suitable for the present purpose, although other equivalent constructions of tube pumps, which ensure reliable clamping of the tubes without overstraining tube material, may be employed.

Figure 4:
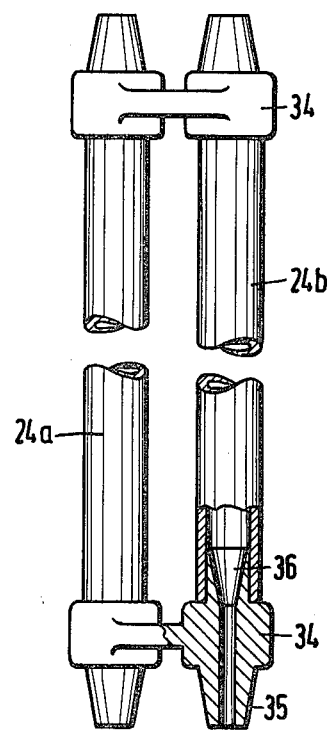
FIG. 4 shows a prefabricated double pump-tube unit.

An important factor in minimising the difference in the pumping capacity of the two halves of the pump is to have the greatest possible agreement between the dimensions and material properties of the two pump tubes. It is also desirable for the two tubes to be placed in the head of the pump in the most uniform and defined way possible. In an embodiment of the invention which takes these points into account, the two pump tubes are in form of a prefabricated unit, as shown e.g. in simplified form in FIG. 4. Such a unit comprises two pieces of tubing 24a and 24b of equal length, which are cut off the tubing material in immediate succession. Thus it can be assumed that, by virtue of the identical manufacturing conditions, the dimensions and material properties of the two tubes will agree very exactly. The two tubes are connected to two end pieces 34, e.g. by adhesion or other common joining methods, and any torsion is avoided. The end pieces may e.g. have conically shaped connecting lips 35 to establish the connection to the rest of the tube system. A prefabricated unit of this type, even if handled less carefully, ensures that the two tubes are inserted very uniformly in the head of the pump, since the end pieces 34 cannot allow either different longitudinal extension or torsion of the tubes. By applying the measures mentioned, the error in drawing up a balance between the two streams of fluid to be brought into agreement can be kept very small. Measurements of a system of this type have shown that, under routine conditions, differences may typically be of the order of 0.02 to 0.05%. There is thus still a considerable margin of safety from the allowable error limit mentioned.

Although the invention has been described with reference to specific example embodiments, it will be appreciated, that it is intended to cover all modifications and equivalents within the scope of the appended claims.

What is claimed is:

1. An apparatus for periodically rinsing a body cavity of a patient, comprising catheter means for insertion into the body cavity, feed container means (4) for gravity flow of liquid into the body cavity, supply container means (2), first pump means (1a) having a given feed capacity, first conduit means operatively connecting said first pump means (1a) to said supply container means (2) and to said feed container means for filling said feed container means from said supply container means through said first pump means, second conduit means operatively connecting said feed container means to said catheter means, second pump means (1b) having the same feed capacity as said given feed capacity of said first pump means, third conduit means operatively connecting said catheter means to said second pump means (1b) for discharging liquid from said body cavity, said first and second pump means comprising respective hose pump means and drive means arranged for driving said hose pump means periodically in unison, measuring chamber means (9) serially connected in said third conduit means, and separate excess flow discharge means operatively connected to said third conduit means upstream of said second pump means, and actuating means operatively connected to said separate flow discharge means whereby the latter are activatable in response to stopping of said first and second pump means.

2. The apparatus of claim 1, wherein said separate excess flow discharge means comprise third pump means operatively connected in parallel to said second pump means, and wherein said actuating means comprise drive means operatively connected to said third pump means.

3. The apparatus of claim 2, wherein said third pump means (13) comprise a hose pump.

4. The apparatus of claim 1 or 2, further comprising measuring means (14) operatively connected to said excess flow discharge means for measuring the quantity of withdrawn excess liquid.

5. The apparatus of claim 1, wherein said first, second and third conduit means comprise flexible hose means and wherein said excess flow discharge means comprise hose clamping valve means operatively connected to said third hose conduit means.

6. The apparatus of claim 1, further comprising filling level sensor means (7) operatively arranged for sensing the filling level of said feed container means.

7. The apparatus of claim 1, wherein said measuring chamber means (9) comprise filling level sensor means operatively arranged to ascertain a filling level or levels in said measuring chamber means.

8. The apparatus of claim 7, wherein said level sensor means produce a signal for stopping said first and second pump means and for simultaneously starting said excess flow discharge means.

9. The apparatus of claim 1, wherein said first and second hose pump means constitute a twin hose pump with two teamed or ganged hose elements (24a, 24b) both of which are made of the same material, have the same lengths, the same diameter, the same wall thickness, and the same elasticity.

10. The apparatus of claim 9, further comprising two end pieces operatively holding together said hose elements, said end pieces comprising connector nipple means for said conduit means.

* * * * *